United States Patent
Charmot et al.

(10) Patent No.: US 6,667,376 B2
(45) Date of Patent: Dec. 23, 2003

(54) CONTROL AGENTS FOR LIVING-TYPE FREE RADICAL POLYMERIZATION AND METHODS OF POLYMERIZING

(75) Inventors: Dominique Charmot, Campbell, CA (US); Han-Ting Chang, Livermore, CA (US); Manikandan Jayaraman, San Francisco, CA (US); Victor Nava-Salgado, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/104,740

(22) Filed: Mar. 22, 2002

(65) Prior Publication Data

US 2003/0204034 A1 Oct. 30, 2003

(51) Int. Cl.$^7$ .................................................. C08F 2/00
(52) U.S. Cl. ........................ 526/220; 526/204; 526/217; 526/222
(58) Field of Search ................................ 526/204, 217, 526/220, 222

(56) References Cited

U.S. PATENT DOCUMENTS

| | | | | |
|---|---|---|---|---|
| 5,314,962 A | * | 5/1994 | Otsu et al. ................... | 525/280 |
| 5,489,654 A | * | 2/1996 | Clouet ......................... | 525/398 |
| 5,658,986 A | * | 8/1997 | Clouet ......................... | 525/88 |
| 5,866,047 A | * | 2/1999 | Nagino et al. .............. | 264/1.27 |
| 6,153,705 A | | 11/2000 | Corpart et al. .............. | 525/244 |

FOREIGN PATENT DOCUMENTS

| | | | | |
|---|---|---|---|---|
| EP | 0349232 | * | 1/1990 | |
| EP | 0421149 | * | 4/1991 | |
| EP | 0449619 | * | 10/1991 | |
| WO | WO 98/10478 | | 1/1998 | ............. C08F/2/38 |
| WO | WO 98/58974 | | 12/1998 | ......... C08F/293/00 |
| WO | WO 99/31144 | | 6/1999 | ............. C08F/2/38 |
| WO | WO 99/35177 | | 7/1999 | ......... C08F/293/00 |
| WO | WO 00/75207 | | 12/2000 | ......... C08F/293/00 |
| WO | WO 02/09409 | | 11/2002 | ......... C08F/293/00 |

OTHER PUBLICATIONS

Hansch et al. *Exploring QSAR: Hydrophobic, Electronic, and Steric Constants* (ACS Professional Reference Book, 1995.

Houben–Weyl, Methoden der organischen Chemie, vol. XIV/1, Makromolekulare Stoffe, Georg–Thieme Verlag, Stuttgart, 1961, pp. 192 to 208.

Houben–Weyl, Methoden der organischen Chemie, vol. XIV/1, Makromolekulare Stoffe, Georg–Thieme–Verlag, Stuttgart, 1961, pp. 411 to 420.

The Chemistry Of Free Radical Polymerization, G.Moad, D.H.Solomon, Eds. (Pergamon Pub., 1995), p 176–183.

\* cited by examiner

*Primary Examiner*—Helen L. Pezzuto

(57) ABSTRACT

Control agents that have an oxygen-nitrogen bond covalently bonded to a thiocarbonyl moiety are provided for living-type free radical polymerization of a wide variety of monomers, particularly vinyl monomers.

19 Claims, No Drawings

CONTROL AGENTS FOR LIVING-TYPE FREE RADICAL POLYMERIZATION AND METHODS OF POLYMERIZING

FIELD OF THE INVENTION

The present invention relates to new compounds useful in assisting in the polymerization of monomers in a free radical polymerization that has living-type kinetics. Polymers made with the control agents and processes for polymerization are also included.

BACKGROUND OF THE INVENTION

The use and mechanism of control agents for free radical polymerization is now generally known; see for example U.S. Pat. No. 6,153,705, WO 98/01478, WO 99/35177, WO 99/31144, and WO 98/58974, each of which is incorporated herein by reference. Despite this knowledge, there remains a need for new agents that may lead to a commercializable process. In particular, control agents that work to control the polymerization of vinyl monomers are of interest. In this context, vinyl monomers are typically monomers with a radically polymerizable double bond not conjugated to any other double bonds such as C=C, C=O or C≡N. Typical examples of vinyl monomers include vinyl acetate, vinylformamide, vinyl pyrrolidone and olefins (such as α-olefins).

The control agents described in WO 98/01478, WO 99/35177, WO 99/31144, and WO 98/58974 generally operate according to a reversible addition-fragmentation transfer mechanism, which confers a "living" character to the free radical polymerization of ethylenic monomers. These control agents, however have not been known to show control of the polymerization of vinyl monomers, such as vinyl acetate. Typically, when using the known control agents with vinyl monomers, the polymerization reaction is either unacceptably slow (e.g., an inhibition effect is observed) or uncontrolled.

In U.S. Pat. No. 6,153,705, control agents of the xanthate type (for instance, CH(CH3)(CO$_2$Et)S—C(=S)OEt) are disclosed that may at least partially control the polymerization of vinyl acetate. However, even partial loss of control is undesirable for certain applications.

This invention provides control agents that unexpectedly provide superior control in the polymerization of vinyl monomers in comparison to known control agents. In particular these new control agents give a narrower molecular weight distribution when compared with known control agents, and, as opposed to the latter, they show a continuous decrease in the polydispersity as the monomer conversion increases. These modified properties allow for improved conditions of the polymerization process and/or improved properties of the polymers obtained from the processes. These control agents showed unexpectedly good results in the control polymerization of vinyl type monomers, such as vinyl acetate, vinylformamide, vinyl pyrrolidone and ethylene.

SUMMARY OF THE INVENTION

This invention provides control agents that are have an O—N bond covalently bonded to a thiocarbonyl moiety. In some embodiments the control agents can be characterized by the general formula:

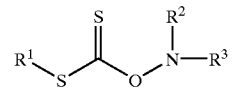

wherein $R^1$ is generally any group that is sufficiently labile to be expelled as its free radical form; $R^2$ and $R^3$ are each independently selected from the group consisting of hydrogen, hydrocarbyl, substituted hydrocarbyl, heteroatom-containing hydrocarbyl, and substituted heteroatom-containing hydrocarbyl, and combinations thereof, and optionally, $R^3$ combines with $R^2$ to form a ring structure, with said ring having from 3 to 50 non-hydrogen atoms.

Another aspect of this invention is directed toward multi-functional control agents, so that the control agents may occupy either a central portion of a polymer chain and/or two or more ends of a polymer. In those embodiments where the control agent occupies a central portion of the polymer backbone, the oxygen-nitrogen bond provides the unique opportunity to degrade the polymer backbone into smaller pieces by external stimuli (e.g., heat, chemical reaction, irradiation, etc.). Such a process is unique as compared to known free radical polymerization and "living" free radical polymerization techniques. In addition, some of the multi-functional control agents are cyclic, which provide the unique opportunity to prepare block copolymers with reduced processes steps. Furthermore, some multi-functional control agents allow for ring opening polymerizations, which heretofore have not found commercial applications in free radical polymerization.

In another aspect, this invention provides control agents that are easy to prepare and economically useful on a commercial scale (e.g., batch, semi-batch or continuous).

Other aspects of this invention include certain of the control agents, which are novel compounds. Polymerization processes using all of the control agents of this invention and polymers that can be made with the control agents of this invention are additional aspects of this invention. In particular, the control agents of this invention provide living-type kinetics and as such allow for the preparation of desired products, including block polymers, star architectures, grafts and hyperbranched polymers.

Thus, it is an object of this invention to provide novel control agents for a living-type free radical polymerization process.

It is another object of this invention to provide novel compounds, which are useful as control agents in a free radical polymerization process.

It is a further object of this invention to provide a novel system for free radical polymerization of monomers that employs living-type kinetics, and in particular for vinyl monomers.

It is still a further object of this invention to polymerize a variety of monomers under commercially acceptable conditions with a family of control agents, and in particular for vinyl monomers.

It is yet a further object of this invention to make controlled architecture polymers with a polymerization process that employs a control agent.

It is further another object of this invention to provide multifunctional control agents that may occupy a central portion of a polymer chain allowing for the polymer chain to be degraded.

Further aspects and objects of this invention will be evident to those of skill in the art upon review of this specification.

DETAILED DESCRIPTION OF THE INVENTION

In the most general terms, the control agents of this invention contain at least one O—N bond covalently bonded to a thiocarbonyl group. In structural terms, the following moiety must be present in the control agents of this invention:

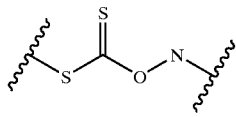

(I)

In describing and claiming the present invention, the following terminology will be used in accordance with the definitions set out below. A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

It is also to be understood that the terminology used herein is for the purpose of describing particular embodiments only, and is not intended to be limiting. As used in this specification and the appended claims, the singular forms "a," "an" and "the" include plural referents unless the context clearly dictates otherwise. In describing and claiming the present invention, the following terminology will be used in accordance with the definitions set out below.

The following definitions pertain to chemical structures, molecular segments and substituents:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different (e.g., $R^2$ and $R^3$ in the structure of formula (1) may all be substituted alkyl groups, or $R^2$ may be hydrido and $R^3$ may be methyl, etc.).

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of one to six carbon atoms, preferably one to four carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom.

The term "alkenyl" as used herein refers to a branched or unbranched hydrocarbon group typically although not necessarily containing 2 to about 24 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 12 carbon atoms. The term "lower alkenyl" intends an alkenyl group of two to six carbon atoms, preferably two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 24 carbon atoms and at least one triple bond, such as ethynyl, n-propynyl, isopropynyl, n-butynyl, isobutynyl, octynyl, decynyl, and the like. Generally, although again not necessarily, alkynyl groups herein contain 2 to about 12 carbon atoms. The term "lower alkynyl" intends an alkynyl group of two to six carbon atoms, preferably three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing one to six, more preferably one to four, carbon atoms. The term "aryloxy" is used in a similar fashion, with aryl as defined below.

Similarly, the term "alkyl thio" as used herein intends an alkyl group bound through a single, terminal thioether linkage; that is, an "alkyl thio" group may be represented as —S-alkyl where alkyl is as defined above. A "lower alkyl thio" group intends an alkyl thio group containing one to six, more preferably one to four, carbon atoms.

The term "allenyl" is used herein in the conventional sense to refer to a molecular segment having the structure —CH=C=CH$_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. In particular embodiments, aryl substituents have 1 to about 200 carbon atoms, typically 1 to about 50 carbon atoms, and preferably 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to univalent hydrocarbyl radicals containing 1 to about 30 carbon atoms, preferably 1 to about 24 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alky, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

As used herein the term "silyl" refers to the $-SiZ^1Z^2Z^3$ radical, where each of $Z^1$, $Z^2$, and $Z^3$ is independently selected from the group consisting of hydrido and optionally substituted alkyl, alkenyl, alkynyl, aryl, aralkyl, alkaryl, heterocyclic, alkoxy, aryloxy and amino.

As used herein, the term "phosphino" refers to the group $-PZ^1Z^2$, where each of $Z^1$ and $Z^2$ is independently selected from the group consisting of hydrido and optionally substituted alkyl, alkenyl, alkynyl, aryl, aralkyl, alkaryl, heterocyclic and amino.

The term "amino" is used herein to refer to the group $-NZ^1Z^2$, where each of $Z^1$ and $Z^2$ is independently selected from the group consisting of hydrido and optionally substituted alkyl, alkenyl, alkynyl, aryl, aralkyl, alkaryl and heterocyclic.

The term "thio" is used herein to refer to the group $-SZ^1$, where $Z^1$ is selected from the group consisting of hydrido and optionally substituted alkyl, alkenyl, alkynyl, aryl, aralkyl, alkaryl and heterocyclic.

As used herein all reference to the elements and groups of the Periodic Table of the Elements is to the version of the table published by the Handbook of Chemistry and Physics, CRC Press, 1995, which sets forth the new IUPAC system for numbering groups.

This invention provides novel compounds and control agents useful for the control of free radical polymerization reactions. In general a free radical polymerization is carried out with these control agents by creating a mixture of at least one polymerizable monomer, the control agent and optionally at least one source of free radicals, e.g., an initiator. The source of free radicals is optional because some monomers may self-initiate upon heating. After or upon forming the polymerization mixture, the mixture is subjected to polymerization conditions. Polymerization conditions are those conditions that cause the at least one monomer to form at least one polymer, as discussed herein, such as temperature, pressure, atmosphere, ratios of starting components used in the polymerization mixture, reaction time or external stimuli of the polymerization mixture.

Generally, the control agents of this invention may be characterized by the general formula (I) above. More specifically, the control agents of this invention may be characterized by the general formula:

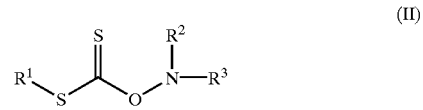

(II)

wherein $R^1$ is generally any group that can be easily expelled under its free radical form ($R^1\bullet$) upon an addition-fragmentation reaction, as depicted below in Scheme 1:

Scheme 1

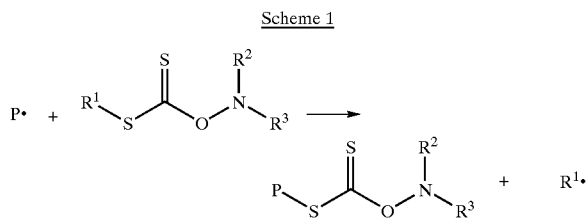

In Scheme 1, P is a free radical, typically a macro-radical, such as polymer chain. More specifically, $R^1$ is selected from the group consisting of hydrocarbyl, substituted hydrocarbyl, heteroatom-containing hydrocarbyl, and substituted heteroatom-containing hydrocarbyl, and combinations thereof. Even more specifically, $R^1$ is selected from the group consisting of optionally substituted alkyl, optionally substituted aryl, optionally substituted alkenyl, optionally substituted alkoxy, optionally substituted heterocyclyl, optionally substituted alkylthio, optionally substituted amino and optionally substituted polymer chains. And still more specifically, $R^1$ is selected from the group consisting of —$CH_2Ph$, —$CH(CH_3)CO_2CH_2CH_3$, —$CH(CO_2CH_2CH_3)_2$, —$C(CH_3)_2CN$, —$CH(Ph)CN$, —$CH(CH_3)CN$, —$CH_2CH_2CH_2CH_3$, and —$C(CH_3)_2Ph$.

Also, $R^2$ and $R^3$ are each independently selected from the group consisting of hydrogen, hydrocarbyl, substituted hydrocarbyl, heteroatom-containing hydrocarbyl, and substituted heteroatom-containing hydrocarbyl, and combinations thereof. More specifically, $R^2$ and $R^3$ may be each independently selected from the group consisting of hydrogen, optionally substituted alkyl, optionally substituted aryl, optionally substituted alkenyl, optionally substituted acyl, optionally substituted, aroyl, optionally substituted alkoxy, optionally substituted heteroaryl, optionally substituted heterocyclyl, optionally substituted alkylsulfonyl, optionally substituted alkylsulfinyl, optionally substituted alkylphosphonyl, optionally substituted arylsulfinyl, and optionally substituted arylphosphonyl. Specific embodiments of $R^2$ and/or $R^3$ are listed in the above definitions, and in addition include perfluorenated aromatic rings, such as perfluorophenyl. Also optionally, $R^2$ and $R^3$ can together form a ring structure, with said ring having from 3 to 50 non-hydrogen atoms. Also optionally, $R^2$ and $R^3$ are joined together to form a double bond optionally substituted alkenyl moiety. Specific embodiments of $R^2$ and $R^3$ are listed in the above definitions.

In those embodiments where the nitrogen atom is part of a heterocycle (i.e., $R^2$ and $R^3$ are joined in a ring structure), the present invention provides increased control over certain other control agents, such as those disclosed in U.S. Pat. No. 6,153,705. In particular, this invention specifies that the nitrogen in the heterocycle be directly bound to the oxygen atom. The control agents of the present invention provide superior control of the polymerization of vinyl monomers as compared to those references that simply refer to any heterocycle. The degree of control of the reaction may be reflected by a narrow molecular weight distribution, also measured by the polydispersity index PDI=Mw/Mn. As is known, the "living" character of the polymerization reaction generally increases as the PDI approaches the ideal value of 1. When the reaction proceeds and conversion increases, usually the PDI decreases and levels off to a plateau value. It is also well accepted that, when the PDI increases as the conversion increases, it is a sign that some side-reaction are taking place. In the case of the polymerization of vinyl acetate controlled by reversible transfer agents of the xanthate type, such a broadening of the molecular weight distribution is noticed as the reaction proceeds (see, U.S. Pat. No. 6,153,705 example 2.34 table 8). Not wishing to be bound to theory, this effect may be due to some deactivation of the "living" chain-ends during the course of the reaction. This "partial" loss of control can also be detrimental when a di-block copolymer is desired; for example, when the first prepared polyvinylacetate block contains deactivated chain ends and a second monomer is added, the deactivated chains do not grow further and might "contaminate" the di-block material. This has unwanted consequences in the use of the resultant polymeric material in specific applications.

Some of the control agents are novel compounds. In some embodiments, the novel compounds may be characterized by the above formula (II). More specifically, novel compounds may be characterized by the formula:

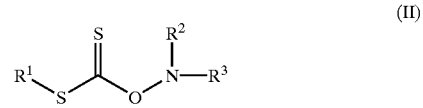

(II)

wherein $R^1$, $R^2$ and $R^3$ are each as defined above, but more specifically where $R^2$ and $R^3$ are independently selected from the group consisting of alkyl, substituted alkyl, aryl and substituted aryl.

In more specific embodiments, the groups of the novel compounds can have $R^1$ is selected from the group consisting of optionally substituted alkyl, optionally substituted aryl, optionally substituted alkenyl, optionally substituted alkoxy, optionally substituted heterocyclyl, optionally substituted alkylthio, optionally substituted amino and optionally substituted polymer chains. Even more specifically, $R^1$ is selected from the group consisting of —$CH_2Ph$, —$CH(CH_3)CO_2CH_2CH_3$, —$CH(CO_2CH_2CH_3)_2$, —$C(CH_3)_2CN$, —$CH(CH_3)CN$, —$CH_2CH_2CH_2CH_3$, —$CH(Ph)CN$ and —$C(CH_3)_2Ph$. Also, $R^2$ and $R^3$ may be each independently selected from the group consisting of hydrogen, optionally substituted alkyl, optionally substituted aryl, optionally substituted alkenyl, optionally substituted acyl, optionally substituted, aroyl, optionally substituted alkoxy, optionally substituted heteroaryl, optionally substituted heterocyclyl, optionally substituted alkylsulfonyl, optionally substituted alkylsulfinyl, optionally substituted alkylphosphonyl, optionally substituted arylsulfinyl, and optionally substituted arylphosphonyl.

Specific control agents within these formulas include:

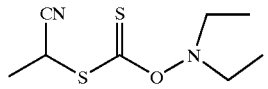

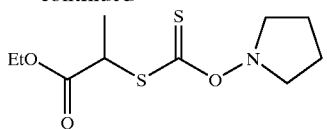
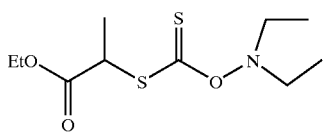
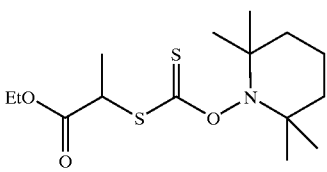
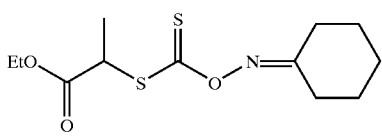
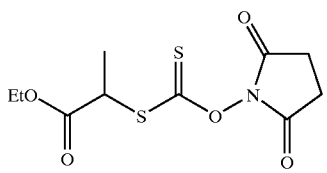
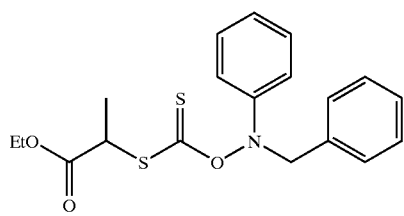
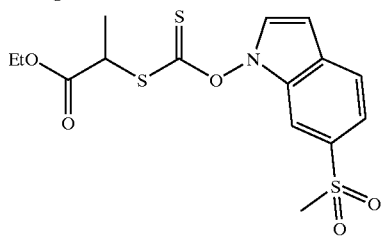

This invention also includes multi-functional control agents and their use in free radical polymerization. A multi-functional control agent is a molecule that allows for two or more polymer chains to polymerize from a single control agent molecule. In some embodiments, the control agents are attached to a core that has multiple functional sites for attachment of one portion of a control agent. Thus, in some embodiments, $R^2$ and/or $R^3$ forms part of or is attached to a core molecule. In other embodiments, $R^1$ is part of or attached to a core molecule. These multi-functional chain transfer agents may be characterized by any of the following general formulas:

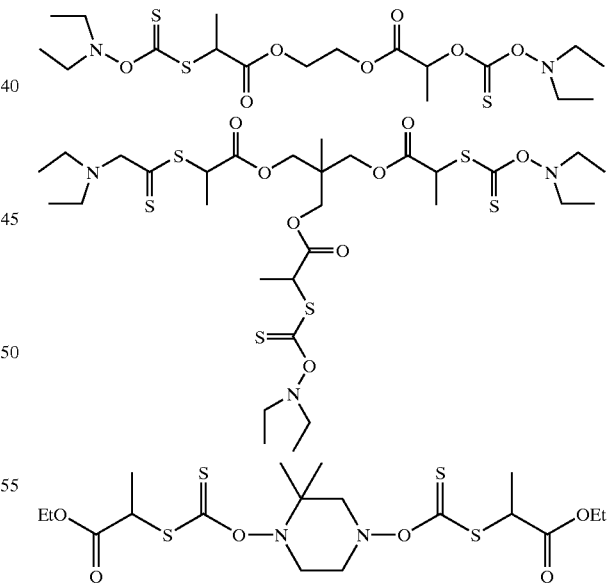

wherein Core is a core molecule, and $R^1$, $R^2$ and R are as defined above, c is 1 or more and d is 2 or more. Formula (IV) can be redrawn substituting $R^2$ for $R^3$, but this would be redundant. Formulas (III) and (IV) include multiple core molecules, providing many possible points from which a free radical polymerization may be controlled. This provides the ability to make may different architectures for polymers, some of which are discussed below. For example, for a star architecture polymer c is 1 and d is 3 for a three arm star; c is 1 and d is 4 for a 4 arm star; c is 1 and d is 6 for a six arm star; etc. Also for example, for a grafted polymer, c is 1 and d is 2 for two grafts, etc. For a hyper-branched polymer, c is 2 or more and d is 2 or more.

The multifunctional chain transfer agents may also be drawn for the more specific embodiments of this invention, as follows:

The Core molecule may be selected from the group consisting of dendritic molecules, small molecules and polymers with at least two terminus ends. Thus, Core molecule may be optionally substituted hydrocarbyl and optionally substituted heteroatom containing hydrocarbyl. Specific examples of Core molecules include:

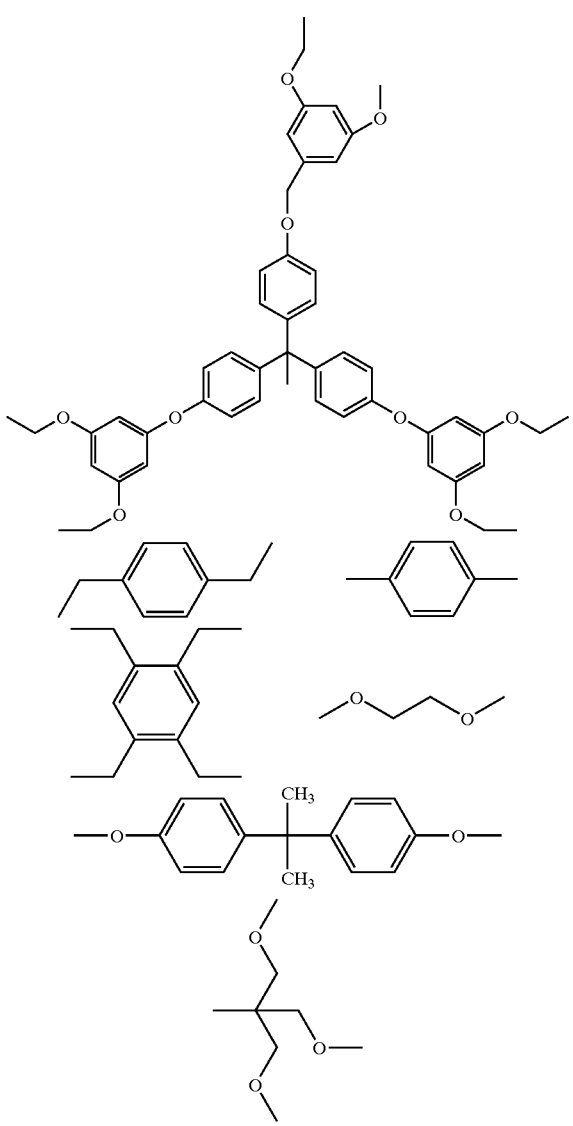

In other embodiments, the Core will be a polymer chain. These embodiments allow for the preparation of grafts or block copolymers by attaching control agents to two or more points along the polymer backbone or side chains or polymer termni.

In alternative embodiments, the control agents of this invention have a ring structure, which upon ring opening may form a multi-functional control agent. Thus, in some embodiments, $R^3$ is deleted, and the nitrogen atom from which $R^3$ was deleted forms a ring with $R^1$ providing general formula:

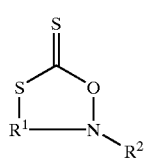

(V)

wherein the above variables have the same definitions, with the exception that $R^1$ is a bifunctional moiety within the definitions given above. Note that $R^1$ can contribute more than one atom to the ring backbone, and thus the ring backbone can have 5, 6 or more atoms. In a particularly preferred embodiment, $R^1$ comprises —CH($R^5$)—C(O)— wherein $R^5$ is selected from the group consisting of hydrogen, hydrocarbyl, substituted hydrocarbyl, heteroatom-containing hydrocarbyl, and substituted heteroatom-containing hydrocarbyl, and combinations thereof. In particular, $R^5$ is selected from the group consisting of hydrogen, optionally substituted alkyl, optionally substituted aryl, optionally substituted alkenyl, optionally substituted acyl, optionally substituted, aroyl, and optionally substituted alkoxy. Preferred $R^1$ groups include hydrogen, methyl, ethyl, propyl, butyl, methoxy, ethoxy, propoxy, phenoxy and phenyl.

The multifunctional chain transfer agents may also be drawn for the more specific embodiments of this invention, as follows:

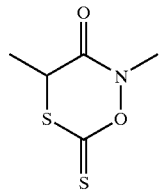

The control agents of this invention are synthesized, generally, by methods known to those of skill in the art. Two synthetic approaches are shown in the following scheme 2 and scheme 3:

Scheme 2

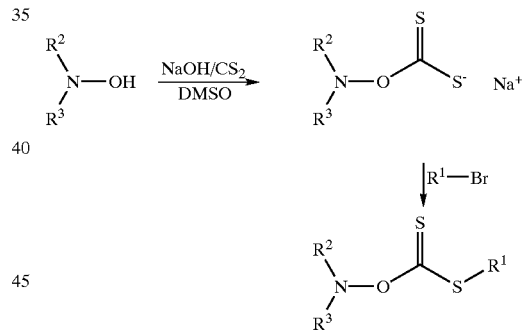

Scheme 3

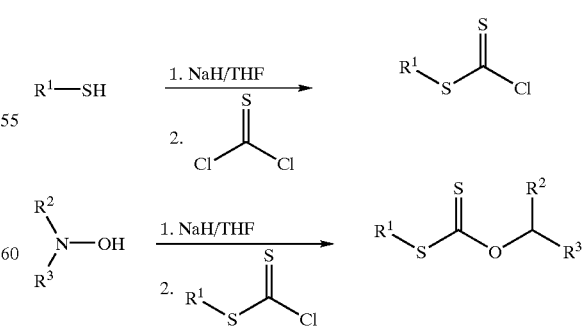

For the Scheme 2 approach, the synthesis conditions optimized for these particular nucleophiles—hydroxyamines and their derivatives include: temperature in the range of 0° C. to ambient; solvents—acetone, acetonitrile, dioxane, DMF, DMSO; base—sodium hydroxide, potassium hydroxide, and sodium hydride. The preferred conditions include using sodium hydroxide as the base in DMSO at ambient temperature.

The general procedure comprises starting with the hydroxyamine or its derivative dissolved in DMSO in approximately a 0.5–1.0 M concentration at ambient temperature. The solution is then treated with approximately 1 equivalent of NaOH and followed by addition of approximately 1 equivalent of carbon disulfide. The resulting solution is then stirred (for example, for approximately 1 hour at ambient temperature) before addition of approximately 1 equivalent of an alkylation agent.

For the Scheme 3 approach, the general procedure comprises generating dithiocarbonyl chloride and then coupling it with hydroxylamine, as follows. A mercaptan was treated with approximately one equivalent of sodium hydride to form the corresponding thiolate in anhydrous THF solvent. Subsequently, to this reaction mixture approximately one equivalent of thiophosgen was added and stirred for approximately one hour, then followed by addition of approximately one equivalent of sodium hydride-deprotonated hydroxylamine.

Work-up may comprise addition of water, extraction with organic solvent, and drying. The desired control agent may be purified by chromatography and/or distillation and may be characterized by $^1$H NMR, $^{13}$C NMR, and LC/MS.

The polymerization conditions that may be used include temperatures for polymerization typically in the range of from about 20° C. to about 110° C., more preferably in the range of from about 40° C. to about 90° C. and even more preferably in the range of from about 50° C. to about 80° C. The atmosphere may be controlled, with an inert atmosphere being preferred, such as nitrogen or argon. The molecular weight of the polymer is controlled via adjusting the ratio of monomer to control agent. Generally, the molar ratio of monomer to control agent is in the range of from about 5 to about 5000, more preferably in the range of from about 10 to about 2000, and most preferably from 10 to about 1500.

A free radical source is provided in the polymerization mixture, which can stem from spontaneous free radical generation upon heating or preferably from a free radical initiator. In the latter case the initiator is added to the polymerization mixture at a concentration high enough to for an acceptable polymerization rate (e.g., commercially significant conversion in a certain period of time, such as listed below). Conversely, a too high free radical initiator to control agent ratio will favor unwanted dead polymer formation through radical-radical coupling reaction leading to polymer materials with uncontrolled characteristics. The molar ratio of free radical initiator to control agent for polymerization are typically in the range of from about 3:1 to about 0.02:1.

Polymerization conditions also include the time for reaction, which may be from about 0.5 hours to about 72 hours, preferably in the range of from about 1 hour to about 36 hours, more preferably in the range of from about 2 hours to about 18 hours. Conversion of monomer to polymer is preferably at least about 50%, more preferably at least about 75% and most preferable at least about 85%.

The polymerization process generally proceeds in a "living" type manner. Thus, generally an approximately linear relationship between conversion and number average molecular weight can be observed, although this is not a pre-requisite. The living character manifests itself by the ability to prepare block copolymers: hence, a polymer chain is first grown with monomer A, and then, when monomer A is depleted, monomer B is added to extend the first block of polymer A with a second block of polymer B. Thus, in some instances, particularly when the chain transfer constant of the control agent, Ct, is low (Ct being defined as the ratio of the transfer rate coefficient to the propagation rate constant), e.g., Ct less than 2, the molecular weight to conversion plot might not exhibit a linear trend: this does not preclude however that block copolymer formation did not occur. Block copolymer formation through a living process can be demonstrated using analytical techniques such as polymer fractionation with selective solvent (of polymer A, polymer B, respectively), gradient elution chromatography and/or 2-dimensional chromatography. Block copolymers tend to microphase-separate and organize in a variety of morphologies that can be probed by physical techniques such as X-ray diffraction, dynamic mechanical testing, and the like.

Initiators, as discussed above, may be optional. When present, initiators useful in the polymerization mixture and the inventive process are known in the art, and may be selected from the group consisting of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, and azo compounds. Specific initiators include benzoylperoxide (BPO) and AIBN. The polymerization mixture may use a reaction media is typically either an organic solvent or bulk monomer or neat. Optionally, after the polymerization is over (e.g., completed or terminated) the thio-moiety (e.g., a dithio-moiety) of the control agent can be cleaved by chemical or thermal ways, if one wants to reduce the sulfur content of the polymer and prevent any problems associated with presence of the control agents chain ends, such as odor or discoloration. Typical chemical treatment includes the catalytic or stoichiometric addition of base such as a primary amine, acid or anhydride, oxidizing agents such as hypochlorite salts, or reducing agents such as Raney nickel.

Generally, monomers that may be polymerized using the methods of this invention (and from which M, below, may be derived) include at least one monomer is selected from the group consisting of styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate and combinations thereof. Functionalized versions of these monomers may also be used. Specific monomers or comonomers that may be used in this invention include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-30 butylmethacrylamide, N-methylolmethacrylamide, N-ethylolmethacrylamide, N-tert-butylacrylamide, N-n-butylacrylamide, N-methylolacrylamide, N-ethylolacrylamide, 4-acryloylmorpholine, vinyl benzoic acid (all isomers), diethylaminostyrene (all isomers), α-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, isoprene, chloroprene, ethylene, vinyl acetate and combinations thereof.

In some embodiments of the polymers of this invention, a combination of hydrophobic and hydrophilic monomers may be used, either randomly or in separate blocks of a copolymer (e.g., thermoplastic elastomers, grafts, etc). The hydrophobic/hydrophilic nature of monomers may be determined according to the log P of the particular monomers, which is sometimes referred to as the octanol-water partition coefficient. Log P values are well known and are determined according to a standard test that determines the concentration of monomer in a water/1-octanol separated mixture. In particular, computer programs are commercially available as well as on the internet that will estimate the log P values for particular monomers. Some of the log P values in this application were estimated from the web site http://esc.syrres.com/interkow/kowdemo.htm, which provides an estimated log P value for molecules by simply inserting the CAS registry number or a chemical notation. Log P values listed herein were obtained from either the web site listed above or from Hansch et al. *Exploring QSAR: Hydrophobic, Electronic, and Steric Constants* (ACS Professional Reference Book, 1995), which is incorporated herein by reference.

Suitable hydrophilic monomers (with approximate log P values listed in parentheses) may be listed above and include, but are not limited to, acrylic acid (0.35), methacrylic acid (0.93), N,N-dimethylacrylamide (−0.13), dimethyl aminoethyl methacrylate (0.97), quaternized dimethylaminoethyl methacrylate, methacrylamide (−0.26), N-t-butyl acrylamide (1.02), maleic acid (−0.48), maleic anhydride and its half esters, crotonic acid (0.72), itaconic acid (−0.34), acrylamide (−0.67), acrylate alcohols, hydroxyethyl methacrylate, diallyldimethyl ammonium chloride, vinyl ethers (such as methyl vinyl ether), maleimides, vinyl pyridine, vinyl imidazole (0.96), other polar vinyl heterocyclics, styrene sulfonate, allyl alcohol (0.17), vinyl alcohol (such as that produced by the hydrolysis of vinyl acetate after polymerization), salts of any acids and amines listed above, and mixtures thereof. Preferred hydrophilic monomers include acrylic acid, N,N-dimethyl acrylamide (−0.13), dimethylaminoethyl methacrylate (0.97), quatemized dimethyl aminoethyl methacrylate, vinyl pyrrolidone, salts of acids and amines listed above, and combinations thereof.

Suitable hydrophobic monomers may be listed above and include, but are not limited to, acrylic or methacrylic acid esters of $C_1$–$C_{18}$ alcohols, such as methanol, ethanol, methoxy ethanol, 1-propanol, 2-propanol-1-butanol, 2-methyl-1-propanol, 1-pentanol, 2-peritanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol (2-methyl-2-propanol), cyclohexanol, neodecanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-tri methyl-1-hexanol, 1-decanol, 1-dodecanol, 1-hexadecanol, 1-octa decanol, and the like, the alcohols having from about 1 to about 18 carbon atoms, preferably from about 1 to about 12 carbon atoms; styrene; polystyrene macromer, vinyl acetate; vinyl chloride; vinylidene chloride; vinyl propionate; alpha-methylstyrene; t-butylstyrene; butadiene; cyclohexadiene; ethylene; propylene; vinyl toluene; and mixtures thereof. Preferred hydrophobic monomers (with approximate log P values listed in parentheses) include n-butyl methacrylate (2.36), isobutyl methacrylate (2.66), t-butyl acrylate (2.09), t-butyl methacrylate (2.54), 2-ethylhexyl methacrylate (4.09), methyl methacrylate (1.38), vinyl acetate (0.73), vinyl acetamide, vinyl formamide, and mixtures thereof, more preferably t-butyl acrylate, t-butyl methacrylate, or combinations thereof.

In addition, monomers that polymerize in a ring closing method may also be used in this invention, including monomers that are of the formula: $CH_2$=CH—X'—CH=$CH_2$ where X' comprises from 1 to 20 non-hydrogen atoms. Such monomers are well known in the art. A specific example is $\{CH_2$=CH—N(CH_3)_2—CH=CH_2\}^+\{Cl\}^-$.

In the broadest sense, an emulsion polymerization is any heterogeneous polymerization in an aqueous environment.

Typically, these systems produce particles of polymer as product. Those skilled in the art recognize many variants of these heterogeneous polymerizations, including true emulsions, micro emulsions, mini emulsions, suspensions and dispersions. These processes are generally distinguished by differences in process, components or results, with specific factors including the presence, amount and type of surfactant required; presence, amount and type of intitiator; presence, type and amount of monomer, including monomer solubility; polymerization kinetics; temperature; order of addition of the components, including the timing of addition of the components (e.g., monomer); solubility of the polymeric product; agitation; presence of co-solvents; resulting particle size; particle stability in the polymerization system toward coagulation or sedimentation; and other factors known to those skilled in the art. In some embodiments of this invention, systems that employ a shearing force or step to create small particle sizes are excluded.

One specifically preferred embodiment of the invention is a controlled heterogenous polymerization reaction in an emulsion characterized by particle sizes ranging from 20 to 1000 nm, and preferably from 30 to 600 nm or from 40 to 300 nm. Polymerizations of this embodiment may have process parameters similar to those discussed above for "traditional" or "true" emulsion polymerizations. These emulsions are stable (on the order of many months with no observed coagulation or sedimentation), yet are prepared using surfactant in amounts less than 3% by weight to monomer.

The use of control agents under emulsion conditions offers other benefits associated with living kinetics (e.g., linear increase in molecular weight as a function of conversion). The controlled free radical emulsion polymerizations of the invention provide a high degree of control over molecular weight often with narrow molecular weight distribution (polydispersity ($M_W/M_N$) generally less than 2 and preferably between 1.1 and 1.8).

In the heterogeneous polymerization process of this invention, the control agent is combined with water, optionally surfactant, initiator, and at least one monomer. Polymerization conditions include a temperature in the range of from about 25° C. to about 150° C., preferably between about 35° C. and about 110° C., more preferably between about 40° C. and about 100° C., and most preferably between about 50° C. and about 90° C.

Polymerization conditions also include a pressure between about ambient pressure up to about 100 atmospheres. Polymerization conditions also include the time for reaction, which may be from about 0.5 hours to about 72 hours, preferably in the range of from about 1 hour to about 36 hours, more preferably in the range of from about 2 hours to about 18 hours.

Surfactants can be useful in the processes and composition of this invention. Suitable surfactants include any species or mixture of species capable of stabilizing colloidal emulsions. Generally surfactants are amphiphilic molecules comprising both hydrophobic and hydrophilic regions, which are capable of adsorbing to surfaces. Surfactants may be small molecules or polymers, micelle forming or non-micelle forming and may be anionic, cationic, zwitterionic or nonionic. In some embodiments, it may be desirable to use mixtures of surfactants, for example to enhance particle stability or control particle formation. Surfactants can play an important role in determining particle size, particle distribution, particle formation and the stability of the resulting polymer emulsion, which are factors that those of skill in the art typically consider when choosing a surfactant for any specific embodiment. Typical amounts of surfactants range from about 0.01 to about 200% by weight relative to the monomer, with a more preferred range being from about 0.1 to about 5% by weight and more specifically preferred being from about 0.5 to about 3% by weight.

Suitable surfactants include anionic, small molecule surfactants including substituted or unsubstituted hydrocarbyl sulfates, sulfonates, carboxylates, phosphonates and phosphates, having between 6 and 30 carbon atoms per anionic functional group. When the hydrocarbyl group is substituted, it may have one or more hydrogen or carbon atoms replaced with another atom selected from the group consisting of N, S, O, Si, F, Cl, Br and I. The hydrocarbyl may also have one or more hydrogen or carbon atom replaced with a functionality such as a keto, ester, amide, ether, thioether and the like. Specific examples of anionic, non-polymeric surfactants include sodium dodecyl sulfate, sodium dodecylbenzene sulfonate, $C_{14}$–$C_{16}$ α-olefin sulfonate, oleoyl methyltaurine, alkyl sulfosuccinate, sodium stearate, alkyl substituted disulfonated diphenyloxide and nonylphenoxy oligo(ethylene glycol) sulfate. Ionic polymers can be used, including polyethyleneimine, polyacrylic acid, carboxymethyl cellulose and the like. Suitable cationic surfactants include cetyltrimethyl ammonium bromide, N-methyl(4-dodecylpyridinium bromide). Suitable nonionic surfactants include ethoxylated mono-, di- and trialkylphenols (degree of ethoxylation: 3 to 100, alkyl radical: $C_4$ to $C_{12}$), ethoxylated fatty alcohols (degree of ethoxylation: 3 to 100, preferably 6 to 50, alkyl radical: $C_6$ to $C_{20}$) and alkali metal and ammonium salts of alkylsulfates (alkyl radical: $C_8$ to $C_{18}$), of sulfuric half-esters of ethoxylated alkanols (degree of ethoxylation: 1 to 70, in particular 2 to 10, alkyl radical: $C_{10}$ to $C_{18}$) and of ethoxylated alkylphenols (degree of ethoxylation: 3 to 100, preferably 6 to 50, alkyl radical: $C_4$ to $C_{18}$) and alkali metal and ammonium salts of alkanesulfonic acids (alkyl radical: $C_{10}$ to $C_{18}$) and of alkylarylsulfonic acids (alkyl radical: $C_9$ to $C_{18}$). Further suitable surfactants, such as sulfosuccinates, are described in Houben-Weyl, Methoden der organischen Chemie, Volume XIV/1, Makromolekulare Stoffe, Georg-Thieme Verlag, Stuttgart, 1961, pages 192 to 208. Alternative surfactants include functional monomers, polymerizable surfactants and water-soluble surface-active polymers, including block copolymers, such as polyethyleneoxide-b-polypropyleneoxide-b-polyethyleneoxide (Pluronic®). Specific examples include polyvinyl alcohols, cellulose derivatives or vinylpyrrolidone-containing copolymers. A detailed description of further suitable protective colloids is given in Houben-Weyl, Methoden der organischen Chemie, Volume XIV/1, Makromolekulare Stoffe, Georg-Thieme-Verlag, Stuttgart, 1961, pages 411 to 420. Currently commercially available surfactants that are useful in this invention are listed below in Table 1.

TABLE 1

| Trade Name | Supplier | Contents |
| --- | --- | --- |
| Ionics | | |
| Abex VA-50 | Rhodia | 46%; 1:1 mix of anionic and ethoxylated octyl phenol |
| Abex 2020 | Rhodia | Anionic/non-ionic mix (APE free), 30% |
| Abex 2030 | Rhodia | Anionic/non-ionic mix (APE free), 30% |
| Abex 18-S | Rhodia | Na Ether Sulfates; APE-free, 35% |
| Abex 12-S | Rhodia | Na Ether Sulfates; APE-free, 30% |
| Aerosol OT | Sigma | [(Bis-2-ethylhexyl)sodium sulfosuccinate], $C_{20}H_{37}O_7S.Na$, $M_w$ 444.6, 10% |
| Aerosol 22 | Sigma | [(Bis-2-ethylhexyl)sodium sulfosuccinate], $C_{20}H_{37}O_7S.Na$, $M_w$ 444.6, neat d = 1.12 |
| Calfax DB-45 | Pilot Chemical | $C_{12}$ (branched) Sodium diphenyloxide disulfonate, 45% |
| Calfax 16L-35 | Pilot Chemical | $C_{16}$ (linear) Sodium diphenyloxide disulfonate, 35% |
| Calimulse L-30 | Pilot Chemical | Sodium linear alkyl benzene sulfonate 30% |
| Calimulse EM-30 | Pilot Chemical | Sodium branched dodecyl benzene sulfonate 30% |
| Calsoft F-90 | Pilot Chemical | Sodium linear alkyl benzene sulfonate, solid, 90+% |
| Dowfax C6L | Dow | Disulfonated diphenyloxide with $C_6$ backbone |
| Dowfax C10L | Dow | Disulfonated diphenyloxide with $C_{10}$ backbone |
| Dowfax 8390 | Dow | Disulfonated diphenyloxide with $C_{16}$ backbone, 45% |
| Emulgator 825 | BASF | anionic/non-ionic mix |
| Emulgator 825-S | BASF | anionic/non-ionic mix |
| Rhodacal A-246/L | Rhodia | sodium alpha C14–C16 olefin sulfonate (38–41%) |
| Rhodacal DS-4 | Rhodia | sodium dodecyl benzene sulfonate 23% |
| SDS | Aldrich | sodium dodecyl sulfate |
| SDBS | Aldrich | sodium dodecyl benzene sulfonate 90% |
| Triton QS-30 | Union Carbide | 90%, gel like |
| Triton X-200 | Union Carbide | 28% aq dispersion |
| Atphos 3232 | ICI | Polyoxyethylene phosphate ester |
| Atphos 3226 | ICI | anionic sfac, phosphoric acid |
| Atphos 3202 | ICI | NonylPE n = 6, acid form, 100% |
| Nonionics | | |
| Abex 2545 | Rhodia | |
| Abex 2535 | Rhodia | |
| Dynol 604 | Air Products | Ethoxylated acetylenic diols, 100% |
| Igepal CO-210 | Aldrich | APE ($C_9H_{19}$—$C_6H_4$—$(OCH_2CH_2)_2OH$) 100% |
| Igepal CO-520 | Aldrich | APE ($C_9H_{19}$—$C_6H_4$—$(OCH_2CH_2)_5OH$) 100% |
| Igepal CA-897 | Rhodia | APE (octylphenol ethoxylate) 70%, n = 40 |
| Igepal CO-897 | Rhodia | APE (nonylphenol ethoxylate) 70% n = 40 |
| Pluronic F38 | BASF | EO-PO-EO block, average $M_w$ 4700 HLB 31 |
| Pluronic F98 | BASF | EO-PO-EO block, average $M_w$ 13K, HLB 28 |
| Pluronic P65 | BASF | EO-PO-EO block, average $M_w$ 3400 HLB 17 |
| Surfynol 104 PA | Air Products | 50% in isopropyl alcohol, 50% 2,4,7,9-tetramethyl-5-decyne-4,7,-diol |
| Surfynol 104 PG-50 | Air Products | 50% in propylene glycol, 50% 2,4,7,9-tetramethyl-5-decyne-4,7,-diol |
| Surfynol DF-58 | Air Products | silicone-based |
| Surfynol 440 | Air Products | Surfynol 104 with ethylene oxide chains, more hydrophilic, 100% |
| Surfynol 465 | Air Products | Surfynol 104 with ethylene oxide chains, more hydrophobic, 100% |
| Triton X-100 | Union Carbide | t-octylphenoxy-polyethoxyethanol (n = 9.5), 100% |
| Triton X-405 | Union Carbide | t-octylphenoxy-polyethoxyethanol, 70% |

The process of the invention does not necessarily require surfactant. For example, surfactant-free recipes can be used where the sulfate groups on a persulfate initiator impart the latex stability. In this case, relatively large ratios of initiator to monomer are used (e.g., 50:1 to 250:1) and large particles result (e.g., 300–600 nm). The ratios of components (e.g., initiators, surfactants, monomers, and control agents) in the polymerization mixture may be important and can vary widely depending on the particular application. The ratio of monomer to control agent can be used to determine the molecular weight of polymers produced using the controlled heterogerieous free radical polymerization processes of the invention. According to these processes, the number average molecular weight of the resulting polymers depends linearly on the number of control agents in the polymerization and the mass of monomer.

In some embodiments, the monomer to initiator ratio may be in the range of from about 10:1 to about 10,000:1, more preferably the range of from about 50:1 to about 10,000:1 and most preferably the range of from about 100:1 to about 5000:1. Another ratio that may be controlled is the ratio of equivalents of initiator to control agent, (with the assumption that the amount of initiator is approximately equivalent to the number of radical produced), which is typically in the range of from about 1:0.1 to about 1:10, more preferably the range of from about 1:0.3 to about 1:5 and most preferably the range of from about 1:0.4 to about 1:2. When a redox system is used, it may be present the ratio of initiator to reductant typically in the range of from about 1:0.1 to about 1:4, more preferably the range of from about 1:0.3 to about 1:2 and most preferably the range of from about 1:0.4 to about 1:1.6. The surfactant to monomer ratio may be controlled and is typically in the range of from about 0.0001 to about 2:1, more preferably the range of from about 0.001:1 to about 0.05:1 and most preferably the range of from about 0.001:1 to about 0.02:1 (although for some emulsions there may be no surfactant added at all where other reaction components perform that function). The percent solids may be in the range of from 0.001% to about 90% by volume. In some preferred applications, the novel aqueous polymer emulsions are produced with a solids content of=40%, advantageously=50%, by volume, based on the total aqueous polymer emulsion. The useful solids content for other applications is from 0.5 to 75% by volume. The preparation of the novel aqueous polymer emulsions is carried out according to the product by process definition of the subject according to the invention, as stated at the outset, i.e., by the free radical aqueous emulsion polymerization method in the presence of surface active materials and free radical polymerization initiators. The ratio of the aqueous phase to the total amount of the monomers used in both stages is chosen according to the desired solids content of the aqueous polymer emulsion to be prepared.

The emulsion process can be implemented in a batch, semi-batch or continuous mode. In one embodiment the reaction is operated in such a way as to convert the control agent into dormant chains early in the process. For example, the consumption of the control agent is substantially completed when the cumulative monomer conversion (defined as the ratio monomer converted at time t to the total monomer present in the recipe) is less than about 30%, more specifically less than about 20% and even more specifically less than about 10%. This can be performed by adjusting polymerization process variables, such as the sequence and feed-rate of addition of monomers, control agents, initiators, etc. For example, in a semi-batch polymerization process where a fraction of the monomer is introduced initially in the reactor and the remaining fraction fed over a period of time, the control agent is preferentially added in totality in the initial charge. In a continuous polymerization process (e.g., using either a recirculation loop or a series of continuously stirred tank reactors), the control agent is preferably fed in the upstream part of the continuous process. A preferred polymerization process is semi-batch, with the totality of the control agent fed to the initial charge and where the feed rate of the monomer stream is adjusted to a "starved feed regime", i.e., where the monomer to polymer ratio is maintained below 0.2, preferably 0.05, until the control agent is totally consumed (as measured by gas or liquid chromatography). Process variables that may coincide to control the monomer to polymer ratio are rate of monomer additions, initiator to monomer ratios, temperature and particle size.

A free radical source is provided in the polymerization mixture, which can stem from spontaneous free radical generation upon heating or preferably from a free radical initiator. In the latter case the initiator is added to the polymerization mixture at a concentration high enough to for an acceptable polymerization rate (e.g., commercially significant conversion in a certain period of time, such as listed below). Conversely, a too high free radical initiator to control agent ratio will favor unwanted dead polymer formation through radical-radical coupling reaction leading to polymer materials with uncontrolled characteristics. The molar ratio of free radical initiator to control agent for polymerization are typically in the range of from about 2:1 to about 0.02:1.

The polymers formed with the chain transfer agents of this invention are believed to be grown via a degenerative transfer mechanism. Thus, upon analysis of the obtained polymers, monomers might appear between the $R^1$—S bond, and any of the above formulas can be rewritten in a polymeric form. For example, the polymers of this invention may be characterized by the general formula:

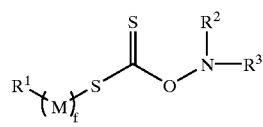
(VI)

wherein M is a monomer or mixture of monomers or at least 2 blocks of different monomer (any from the above lists) and f is the degree of polymerization, and $R^1$, $R^2$ and $R^3$ are as defined above.

Free radical polymerization of cyclic monomers by ring opening mechanism is known (see, e.g., The Chemistry Of Free Radical Polymerization, G. Moad, D. H. Solomon, Eds. (Pergamon Pub., 1995), p 176–183). However no commercially viable process has been developed so far. This is due at least in part to the poor reactivity of these monomer compounds (e.g., Ketene acetals) as well as their relative instability to water traces. Moreover, known polymerization mechanisms for ring opening polymerization systems are not know for their living-type kinetics.

The cyclized forms of the multi-functional control agents (such as those described by formulas (V)) typically lead to ring opening reaction under polymerization conditions. The polymer thus formed may be characterized by the general formula:

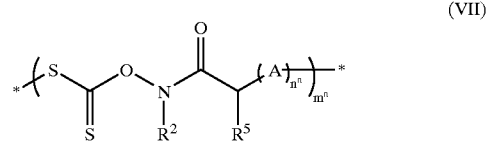
(VII)

where $R^2$ and $R^5$ have the same definitions given above and A represents a repeat unit of block of monomer A (with n" being the degree of polymerization of the block; m" being the number of repeat units of the block with the attached control agent; and * representing the ends of the polymer). The molecular weight of the polymer formed from monomer A is generally controlled by controlling the monomer to control agent ratio in the polymerization mixture, as discussed above.

As formula (VII) shown, the multi-functional control agents of this invention also provide, in some embodiments, for a compound (i.e., N—OC(=S)S) in the backbone of a carbon-carbon polymer chain, such as usually obtained by free radical polymerization of ethylenic monomers. This is desirable for several applications: for instance, such polymers can be reduced to low molecular weight material by applying external stimuli such as UV, light, heat, biochemical or chemical treatment, which are known to cleave thiocarbonylthio linkage. Such polymers could be used as thermoplastics susceptible to degradation by exposure to sunlight, or by enzymatic digestion since it is known that short polymers chains are readily biodegradable.

Moreover, multiblock copolymers $(ABx)_y$ can be obtained in a two-step process, by first preparing a first multiblock homopolymer, denoted $(Ax)_y$, where x represents the N—OC(=S)S moiety and y represents the number of A or AB blocks and y is 2 or more, and then adding monomer B in order to get $(ABx)_y$, which may be characterized by the general formula:

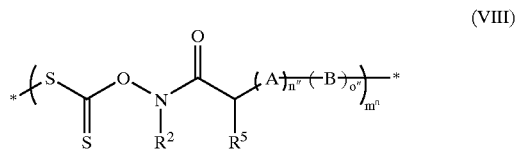
(VIII)

where $R^2$ and $R^5$ and n" and m" have the same definitions given above, A represents a repeat unit of block of monomer A and B represents a repeat unit of block of monomer B and o" is the degree of polymerization of monomer B. Monomers A and B can be selected from any of the above lists. Copolymers having a similar structure as (AB)$_y$ copolymers are usually prepared by multiple sequential addition of different monomers with the usual pitfalls such as loss of control as long as the number of block increase or contamination of block A with B monomers. This new process alleviates these difficulties.

The formulas for multifunctional control agents can also be written in polymer form, as follows:

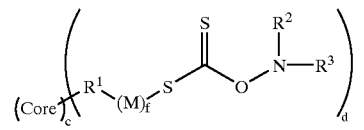

(IX)

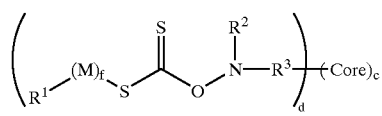

(X)

wherein each of the variable in formulas (IX) to (X) have the meanings that are stated above.

In some embodiments of this invention, it is desirable to make a block copolymer, such as for example with both hydrophobic and hydrophilic monomers, with these monomers being selected from the above lists. In this case, the monomers M in the above formulas will be A and B or more blocks.

As used herein, "block copolymer" refers to a polymer comprising at least two segments of differing composition; having any one of a number of different architectures, where the monomers are not incorporated into the polymer architecture in a solely statistical or uncontrolled manner. Although there may be three, four or more monomers in single block-type polymer architecture, it will still be referred to herein as a block copolymer. In some embodiments, the block copolymer will have an A—B architecture (with "A" and "B" representing the monomers). Other architectures included within the definition of block copolymer include A—B—A, A—B—A—B, A—B—C, A—B—C—A, A—B—C—A—B, A—B—C—B, A—B—A—C (with "C" representing a third monomer), and other combinations that will be obvious to those of skill in the art. Block copolymers can be prepared a number of ways, including sequential addition of monomers or using multi-functional control agents described above. Of course with multi-functional control agents, the control agent may form a linking group between one or more blocks of the copolymers.

In another embodiment, the block copolymers of this invention include one or more blocks of random copolymer together with one or more blocks of single monomers. Thus, a polymer architecture of A—R, A—R—B, A—B—R, A—R—B—R—C, etc. is included herein, where R is a random block of monomers A and B or of monomers B and C. Moreover, the random block can vary in composition or size with respect to the overall block copolymer. In some embodiments, for example, the random block R will account for between 5 and 80% by weight of the mass of the block copolymer. In other embodiments, the random block R will account for more or less of the mass of the block copolymer, depending on the application. Furthermore, the random block may have a compositional gradient of one monomer to the other (e.g., A:B) that varies across the random block in an algorithmic fashion, with such algorithm being either linear having a desired slope, exponential having a desired exponent (such as a number from 0.1–5) or logarithmic. The random block may be subject to the same kinetic effects, such as composition drift, that would be present in any other radical copolymerization and its composition, and size may be affected by such kinetics, such as Markov kinetics. Any of the monomers listed elsewhere in this specification may be used in the block copolymers of this invention.

A "block" within the scope of the block copolymers of this invention typically comprises about 10 or more monomers of a single type (with the random blocks being defined by composition and/or weight percent, as described above). In preferred embodiments, the number of monomers within a single block is about 15 or more, about 20 or more or about 50 or more. However, in an alternative embodiment, the block copolymers of this invention include blocks where a block is defined as two or more monomers that are not represented elsewhere in the copolymer. This definition is intended to encompass adding small amounts of a second monomer at one or both ends of a substantially homopolymeric polymer. In this alternative embodiment, the same copolymer architectures discussed above apply. This definition is therefore intended to include telechelic polymers, which include one or more functional end groups capable of reacting with other molecules. Thus, generally, a telechelic polymer is a block copolymer with in the definitions of this invention. The functional groups present at one or both ends of a telechelic polymer may be those known to those of skill in the art, including, for example, hydroxide, aldehyde, carboxylic acid or carboxylate, halogen, amine and the like, which have the ability to associate or form bonds with another molecule. Likewise, the block copolymers of the invention are intended to encompass telechelic polymers containing bifunctional groups, such as allyl-terminated or vinyl-terminated telechelics, sometimes referred to as macromonomers or macromers because of their ability to participate in polymerization reactions through the terminal functional group.

Combining the above embodiments provides a particularly powerful method of designing block copolymers. For example, a block copolymer may have the architecture F—A—B—F, where F represents functional groups that may be the same or different within a single F—A—B—F structure (which, therefore, may encompass F—A—B—F'). Other block copolymer architectures within the scope of this invention include A—R—B—F and F—A—R—B—F. Other architectures will be apparent to those of skill in the art upon review of this specification—indeed, without wishing to be bound by any particular theory—it is the living nature of the emulsions of this invention that provide the ability to even make these novel block copolymers.

In one embodiment, block copolymers are assembled by the sequential addition of different monomers or monomer mixtures to living polymerization reactions. In another embodiment, the addition of a pre-assembled functionalized block (such as a telechelic oligomer or polymer) to a living free radical polymerization mixture yields a block copolymer. Ideally, the growth of each block occurs to high conversion. Conversions are determined by size exclusion chromatography (SEC) via integration of polymer to monomer peak. For UV detection, the polymer response factor must be determined for each polymer/monomer polymerization mixture. Typical conversions can be 50% to 100% for each block. Intermediate conversion can lead to block copolymers with a random copolymer block separating the two or more homopolymer blocks, depending on the relative rates of polymerization and monomer addition. At high conversion, the size of this random block is sufficiently small such that it is less to affect polymer properties such as phase separation, thermal behavior and mechanical modulus. This fact can be intentionally exploited to improve polymerization times for many applications without measurably affecting the performance characteristics of the resulting polymer. This is achieved by intentionally "killing" or terminating the living nature of the polymerization when a desired level of conversion (e.g., >80%) is reached by neutralizing the control agent, for example by introducing acids, bases, oxidizing agents, reducing agents, radical sources, scavengers, etc. In the absence of control agent, the polymerization continues uncontrolled (typically at much higher reaction rates) until the remaining monomer is consumed. Block copolymer can also be created by grafting monomers, monomer mixtures, oligomers or polymers only polymers having multiple available functional groups.

In other embodiments, block copolymers can be prepared by grafting processes, preparation of telechelic polymers, preparation of macromonomers, etc. In these embodiments, at least one polymer segment is derived from a living or controlled process of the invention, while other segments can be derived from any polymerization process, including, for example, controlled or uncontrolled radical polymerization, condensation polymerization, Ziegler-Natta and related processes, Ring-Opening Metathesis Polymerization, ionic polymerization, surface modification or grafting, or other addition or step-growth processes.

Block copolymers allow the combination of potentially diverse polymer properties (such as hard/soft and/or hydrophilic/hydrophobic (amphiphilic) blocks) into a single polymer chain. Hard/soft block copolymers combine segments with significantly different glass transition temperatures $T_g$. A typical hard/soft copolymer pairs a relatively "hard" block (e.g., styrene) with a relatively "soft" block (e.g., butyl acrylate). The resulting materials can possess performance attributes not found in any of the constituent segments. The presence of microphase separation and various phase morphologies in block copolymers is associated with unique performance attributes of many block copolymers. For example, by combining the stiffness or rigidity characteristic of hard materials with the compliance of soft materials, block copolymers may exhibit advantageous properties, such as processability under melt conditions, elasticity, resistance to abrasion and cracking and desired creep characteristics (corresponding to the material's ability to hold its shape under external stresses) depending on morphology, making them appropriate for use as extrudable bulk materials, coatings and separation media. The exact properties of a hard/soft copolymer depend significantly on the difference between the glass transition temperatures of the constituent blocks; accordingly, selection of monomers having glass transition temperatures a particular distance apart can lead to hard/soft block copolymers having particular desired characteristics. Thus, while for one application it may be appropriate to combine blocks having glass transition temperatures that differ by, for example, 20° C., the choice of $T_g$ (and therefore of materials) depends on the application.

Likewise, the amphiphilic block copolymers produced according to the invention display combinations of hydrophobic and hydrophilic properties that make such materials appropriate for use as surfactants or dispersants, scavengers, surface treatments and the like. Different block sizes over all ratios of monomers and molecular weights lead to families of novel compounds, for example thermoplastics, elastomers, adhesives, and polymeric micelles.

Multi-arm or star polymers can be generated using initiators capable of initiating multiple free radical polymerizations under the controlled conditions of the invention. Such initiators include, for example polyfunctional chain transfer agents, discussed above. Following initiation, the growth of each arm is controlled by the same living kinetics described for linear polymers, making it possible to assemble star polymers whose arms include individual homopolymers as well as di, tri or higher order block copolymers. Alternatively, multi-arm polymers are formed by growing end-functionalized oligomers or polymers followed by the addition of a cross-linking monomer such as ethylene glycol diacrylate, divinyl benzene, methylene bisacrylamide, trimetylol propane triacrylate, etc. The small hydrodynamic volume of star polymers produced according to these methods provides properties such as low viscosity, high $M_W$, and high functionality useful in applications such as rheology control, thermosets, and separation media. Similarly, the inclusion of branched or multiple ethylenically unsaturated monomers enables the preparation of graft polymers, again exhibiting the living kinetics characteristic of this invention. The existence of a block copolymer according to this invention is determined by methods known to those of skill in the art, including nuclear magnetic resonance (NMR), measured increase of molecular weight upon addition of a second monomer to chain-extend a living polymerization of a first monomer, microphase separation (e.g., long range order, microscopy and/or birefringence measurements), mechanical property measurements, (e.g., elasticity of hard/soft block copolymers), thermal analysis and chromatography (e.g., absence of homopolymer).

EXAMPLES

General: All reactions were performed in oven-dried glassware under a positive pressure of argon or nitrogen gas. The air- and moisture-sensitive solutions were transferred by means of a syringe into the rubber-septum-capped reaction vessels. Reaction mixtures and chromatographically collected fractions were concentrated on a rotary evaporator (ca. 20° C./20 torr). Commercial grade reagents were used without further purification, except for monomers, which were degassed by applying a nitrogen- or argon-stream for 30 min. Monomer inhibitors were removed by distillation or filtration over Aldrich-inhibitor-remover [9003-70-07]. Polymerization mixtures were carried out and sealed in a glove box under a nitrogen or argon atmosphere, and performed at 60° C. Size Exclusion Chromatography (SEC) was performed using automated GPC systems and different sets of columns and eluents depending on the polarity of the polymers, see Table 2 for the details. In general, SEC was performed in accord with U.S. Pat. Nos. 6,296,771, 6,294, 338, 6,265,226, 6,260,407 and 6,175,409, each of which is incorporated herein by reference. Molecular weight and polydispersity index (PDI) are referred to linear polystyrene standards.

TABLE 2

| Polymer | Column | Eluent | Standard | Detector |
|---|---|---|---|---|
| Polystyrene | PLgel 10 μm 10³Å, 300 × 7.5 mm + | THF | PS (THF) | RI, UV |
| Polybutyl acrylate | PLgel 10 μm 10⁴Å, 300 × 7.5 mm + | | | (290 nm) |
| Polyvinyl acetate | PLgel 10 μm 10⁵Å, 300 × 7.5 mm + | | | |
| Polyvinyl-dodecanoate | PLgel 5 μm Mixed-C, 300 × 7.5 mm | | | |
| Poly-1-vinyl-2-pyrrolidinone | 3 × PLgel 10 μm Mixed-B, 300 × 7.5 mm | DMF + 0.1% TFA | PS (Toluene) | ELSD |
| Polyvinyl formamide | TSK-Gel G4000PW$_{XL}$, 300 × 7.8 mm | H$_2$O. + 0.1% NaNO$_3$ | None | RI-LS |

Monomer conversion was determined by $^1$H-NMR on a Brucker AC 400 (400 MHz) or by GC on a HP-6890 automated system.

Example 1

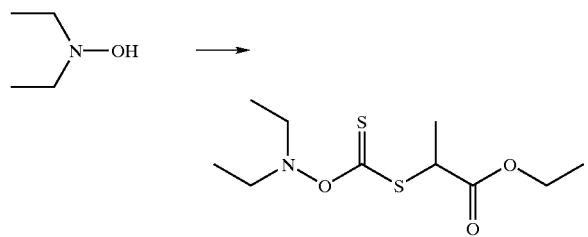

100-mL, two-necked, round-bottomed flask was equipped with an inlet adapter for argon or nitrogen gas and a rubber septum. It was charged with 10 mL of dry DMSO and sodium hydroxide (449 mg, 11.2 mmol), and subsequently diethyl hydroxylamine C'-1 (1.00 g, 11.2 mmol) was administered dropwise by means of a syringe. After 30 min. stirring at room temperature (ca.20° C.), carbon disulfide (854 mg, 11.2 mmol) was added dropwise by means of a syringe over a period of 1 min and stirred for 30 min. Then, the reaction was treated with ethyl 2-bromo-propionate (2.03 g, 11.2 mmol). The resulting reaction mixture was stirred for 12 h and then quenched with 40 mL ice/water. After 5 min, the reaction was extracted with ethyl ether (3×20 mL), the combined organic phases were dried over MgSO$_4$, filtered, and concentrated (ca. 20° C./20 torr). The residue was purified by silica-gel chromatography (hexane:AcOEt, 5:1) to yield 1.70 g of C-1 (83%) as light yellow oil.

Example 2

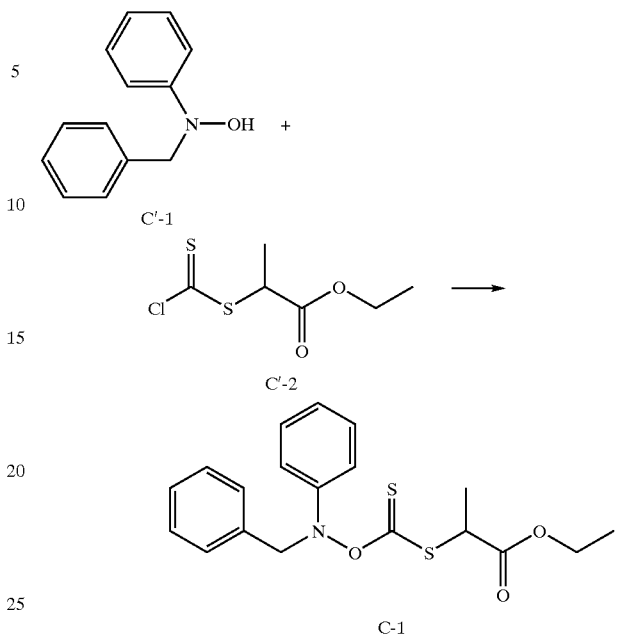

A 250-mL, two-necked, round-bottomed flask was equipped with an inlet adapter for argon or nitrogen gas and a rubber septum. It was charged with 50 mL of dry THF and sodium hydride (286 mg, 11.9 mmol), and subsequently N-benzyl-N-phenyl hydroxylamine C'-1 (2.16 g, 10.9 mmol) in 10 mL THF was administered dropwise by means of a syringe. After 30 min stirring at room temperature (ca. 20' C.), the reaction mixture was transferred dropwise into a septum-capped, 250 mL, two-necked, round-bottomed flask charged with dithiochloroformiate C2' by means of a syringe and syringe-pump over a period of 30 min. The resulting reaction mixture was stirred for 12 h and then quenched with a saturated solution of ammonium chloride aqueous (50 mL). After 5 min, the reaction was extracted with ethyl ether (3×50 mL), the combined organic phases were dried over MgSO$_4$, filtered, and concentrated (ca. 20° C./20 torr). The residue was purified by silica-gel chromatography using the following hexane:dichloromethane eluent gradient (100:0, 75:25, 50:50, 25:75, 0:100) to give 1.41 g of starting material C'-1 (35% conversion) and 1.30 g of product C-1 (99% yield) as light yellow oil.

Examples 3–51

These examples demonstrate the controlled polymerization of vinyl acetate (VA), vinyl pyrrolidone (VP), vinyl formamide (VF), vinyl dodecanoate (VD), styrene (Sty) and butyl acrylate (BA) using the control agents of this invention. Each polymerization was carried out in the same way, a microtiter plate 1 mL vial was charged with control agent, initiator (AIBN) and neat monomer (3.00 mmol) at room temperature (ca. 25° C.). Control agent and initiator ratios were varied as indicated in Table 3. For example, for a degree of polymerization (DP) of 200 with 25% initiator, 3.00 mmol of monomer, 0.015 mmol of control agent and 1.8×10$^{-3}$ mmol of initiator were used. The mixture was then sealed and brought to the reaction temperature 60° C. and let it react for different reaction times. Samples were allowed to cold down to room temperature and then analyzed by GPC and GC or $^1$H-NMR. Results are reported in Table 4, below.

Control Agents

CA-1
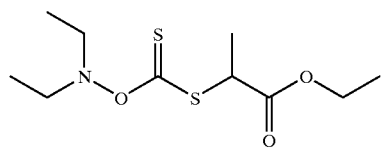

CA-2
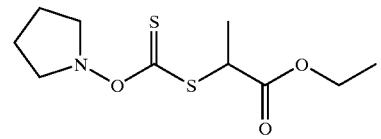

CA-3
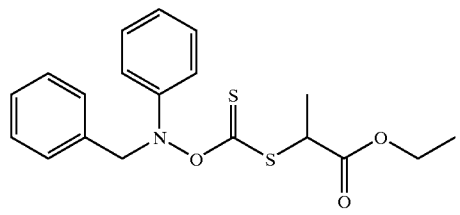

CA-4
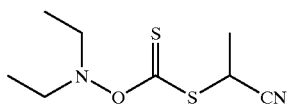

TABLE 3

| Example | Control Agent | Monomer | DP | Initiator (%) | Temp. (° C.) | Time (h) |
|---|---|---|---|---|---|---|
| 3 | CA-1 | VA | 200 | 20 | 60 | 5 |
| 4 | CA-1 | VA | 200 | 20 | 60 | 8 |
| 5 | CA-1 | VA | 200 | 20 | 60 | 12 |
| 6 | CA-1 | VA | 200 | 20 | 60 | 21 |
| 7 | CA-1 | VA | 600 | 20 | 60 | 8 |
| 8 | CA-1 | VA | 600 | 20 | 60 | 12 |
| 9 | CA-1 | VA | 600 | 20 | 60 | 21 |
| 10 | CA-1 | VA | 600 | 20 | 60 | 45 |
| 11 | CA-2 | VA | 200 | 20 | 60 | 2 |
| 12 | CA-2 | VA | 200 | 20 | 60 | 5 |
| 13 | CA-2 | VA | 200 | 20 | 60 | 8 |
| 14 | CA-2 | VA | 200 | 20 | 60 | 12 |
| 15 | CA-2 | VA | 200 | 20 | 60 | 21 |
| 16 | CA-3 | Sty | 200 | 25 | 60 | 9 |
| 17 | CA-3 | Sty | 200 | 25 | 60 | 18 |
| 18 | CA-3 | Sty | 200 | 75 | 60 | 9 |
| 19 | CA-3 | Sty | 200 | 75 | 60 | 18 |
| 20 | CA-3 | BA | 200 | 25 | 60 | 9 |
| 21 | CA-3 | BA | 200 | 25 | 60 | 18 |
| 22 | CA-3 | BA | 200 | 75 | 60 | 9 |
| 23 | CA-3 | BA | 200 | 75 | 60 | 18 |
| 24 | CA-3 | VA | 200 | 25 | 60 | 18 |
| 25 | CA-3 | VA | 200 | 75 | 60 | 9 |
| 26 | CA-3 | VA | 200 | 75 | 60 | 18 |
| 27 | CA-4 | VA | 200 | 25 | 60 | 6 |
| 28 | CA-4 | VA | 200 | 25 | 60 | 12 |
| 29 | CA-4 | VA | 200 | 25 | 60 | 18 |
| 30 | CA-4 | VA | 200 | 25 | 60 | 24 |
| 31 | CA-4 | VA | 200 | 25 | 60 | 45 |
| 32 | CA-4 | VP | 200 | 25 | 60 | 6 |
| 33 | CA-4 | VP | 200 | 25 | 60 | 12 |
| 34 | CA-4 | VP | 200 | 25 | 60 | 18 |
| 35 | CA-4 | VP | 200 | 25 | 60 | 24 |
| 36 | CA-4 | VP | 200 | 25 | 60 | 45 |
| 37 | CA-4 | VD | 200 | 25 | 60 | 6 |

TABLE 3-continued

| Example | Control Agent | Monomer | DP | Initiator (%) | Temp. (° C.) | Time (h) |
|---|---|---|---|---|---|---|
| 38 | CA-4 | VD | 200 | 25 | 60 | 12 |
| 39 | CA-4 | VD | 200 | 25 | 60 | 18 |
| 40 | CA-4 | VD | 200 | 25 | 60 | 24 |
| 41 | CA-4 | VD | 200 | 25 | 60 | 45 |
| 42 | CA-4 | VF | 200 | 25 | 60 | 1 |
| 43 | CA-4 | VF | 200 | 25 | 60 | 1.5 |
| 44 | CA-4 | VF | 200 | 25 | 60 | 2 |
| 45 | CA-4 | VF | 200 | 25 | 60 | 3 |
| 46 | CA-4 | VF | 200 | 25 | 60 | 4 |
| 47 | CA-4 | VF | 200 | 25 | 60 | 6 |
| 48 | CA-4 | VF | 200 | 25 | 60 | 12 |
| 49 | CA-4 | VF | 200 | 25 | 60 | 18 |
| 50 | CA-4 | VF | 200 | 25 | 60 | 24 |
| 51 | CA-4 | VF | 200 | 25 | 60 | 45 |

TABLE 4

Results

| Example | Control Agent | Monomer | Time (h) | Conversion (%) | Mn | PDI |
|---|---|---|---|---|---|---|
| 3 | CA-1 | VA | 5 | 16 | 5965 | 1.83 |
| 4 | CA-1 | VA | 8 | 34 | 7139 | 1.8 |
| 5 | CA-1 | VA | 12 | 63 | 5831 | 1.75 |
| 6 | CA-1 | VA | 21 | 83 | 13880 | 1.48 |
| 7 | CA-1 | VA | 8 | 56 | 17315 | 1.89 |
| 8 | CA-1 | VA | 12 | 81 | 23620 | 1.86 |
| 9 | CA-1 | VA | 21 | 93 | 34723 | 1.8 |
| 10 | CA-1 | VA | 45 | 94 | 38387 | 1.76 |
| 11 | CA-2 | VA | 2 | 72 | 7724 | 1.5 |
| 12 | CA-2 | VA | 5 | 83 | 10621 | 1.56 |
| 13 | CA-2 | VA | 8 | 92 | 16802 | 1.5 |
| 14 | CA-2 | VA | 12 | >95 | 14255 | 1.49 |
| 15 | CA-2 | VA | 21 | >95 | 14931 | 1.48 |
| 16 | CA-3 | Sty | 9 | 13 | 44485 | 1.74 |
| 17 | CA-3 | Sty | 18 | 17 | 58736 | 1.73 |
| 18 | CA-3 | Sty | 9 | 35 | 42216 | 1.8 |
| 19 | CA-3 | Sty | 18 | 45 | 49764 | 1.92 |
| 20 | CA-3 | BA | 9 | 90 | 30028 | 1.86 |
| 21 | CA-3 | BA | 18 | >99 | 29313 | 2.04 |
| 22 | CA-3 | BA | 9 | >99 | 27705 | 1.95 |
| 23 | CA-3 | BA | 18 | >99 | 48245 | 1.73 |
| 24 | CA-3 | VA | 18 | 8 | 2713 | 1.81 |
| 25 | CA-3 | VA | 9 | 36 | 8560 | 1.74 |
| 26 | CA-3 | VA | 18 | 68 | 8905 | 1.56 |
| 27 | CA-4 | VA | 6 | 44 | 8300 | 1.6 |
| 28 | CA-4 | VA | 12 | 90 | 14500 | 1.47 |
| 29 | CA-4 | VA | 18 | 96 | 26100 | 1.38 |
| 30 | CA-4 | VA | 24 | 96 | 17700 | 1.39 |
| 31 | CA-4 | VA | 45 | 96 | 26800 | 1.4 |
| 32 | CA-4 | VP | 6 | 23 | 11280 | 1.13 |
| 33 | CA-4 | VP | 12 | 24 | 11500 | 1.15 |
| 34 | CA-4 | VP | 18 | 27 | 13150 | 1.17 |
| 35 | CA-4 | VP | 24 | 29 | 14000 | 1.19 |
| 36 | CA-4 | VP | 45 | 37 | 15200 | 1.21 |
| 37 | CA-4 | VD | 6 | 6 | 8000 | 1.32 |
| 38 | CA-4 | VD | 12 | 12 | 9350 | 1.35 |
| 39 | CA-4 | VD | 18 | 25 | 11600 | 1.52 |
| 40 | CA-4 | VD | 24 | 29 | 15500 | 1.52 |
| 41 | CA-4 | VD | 45 | 37 | 13000 | 1.6 |
| 42 | CA-4 | VF | 1 | 4 | 11872 | 1.12 |
| 43 | CA-4 | VF | 1.5 | 10 | 19197 | 1.3 |
| 44 | CA-4 | VF | 2 | 29 | 32754 | 1.44 |
| 45 | CA-4 | VF | 3 | 47 | 34581 | 1.44 |
| 46 | CA-4 | VF | 4 | 59 | 32109 | 1.48 |
| 47 | CA-4 | VF | 6 | 77 | 34268 | 1.6 |
| 48 | CA-4 | VF | 12 | 83 | 34767 | 1.63 |
| 49 | CA-4 | VF | 18 | 83 | 35967 | 1.64 |
| 50 | CA-4 | VF | 24 | 86 | 33739 | 1.64 |
| 51 | CA-4 | VF | 45 | 88 | 33262 | 1.64 |

All these results show unambiguously that the control agents provide a living character to the radical polymerization of most common monomers and in particular vinylic monomers such as vinyl acetate, vinyl formamide, vinyl pyrrolidone and vinyl dodecanoate.

Examples 52–63

In the following examples vinyl acetate was polymerized in bulk with AIBN as an initiator at 10 mo-% based on the monomer, and the monomer to control agent ratio is 200:1. Temperature is fixed at 60° C. The experimental conditions are the same as the described in Example 3, above. Examples 52–55 are comparative examples where the control agent is a xanthate of formula CH(CH3)(CO2Et)S—C(=S)OEt taught in U.S. Pat. No. 6,153,705. In example 56–59 and 60–63, the control agent were CA-1 and CA-2, respectively. The results are shown in Table 5, below:

TABLE 5

| Example | Control agent | Conversion (%) | Mn | Mw | PDI |
|---|---|---|---|---|---|
| 52 | Xanthate | 17 | 3132 | 3790 | 1.21 |
| 53 | Xanthate | 59 | 10277 | 13360 | 1.3 |
| 54 | Xanthate | 78 | 14614 | 21483 | 1.47 |
| 55 | Xanthate | 90 | 16620 | 26426 | 1.59 |
| 56 | CA-1 | 16 | 5965 | 10916 | 1.83 |
| 57 | CA-1 | 34 | 7139 | 12850 | 1.8 |
| 58 | CA-1 | 63 | 5831 | 10204 | 1.75 |
| 59 | CA-1 | 83 | 13880 | 20542 | 1.48 |
| 60 | CA-2 | 16 | 5965 | 10916 | 1.83 |
| 61 | CA-2 | 34 | 7139 | 12850 | 1.8 |
| 62 | CA-2 | 63 | 5831 | 10204 | 1.75 |
| 63 | CA-2 | 83 | 13880 | 20542 | 1.48 |

These examples show that the polydispersity index steadily increases as reaction proceeds in the case of the xanthate control agent, in contrast with the trend observed in examples 56–63 with the control agents of the invention.

Examples 64–111

These examples demonstrate the use of the control agents of the invention to control the polymerization of vinyl acetate in an emulsion process.

Polymerizations were carried out in semi-continuous process where vinyl acetate (900 mg, 90% of total monomer) and initiator (90% of total initiator) were in the continuous charge. Xanthate and CT-4 control agents (both at 0.5 mole % to monomer) were used for comparison. The total volume of polymerization was 3 mL in a total 30% solid concentration. The initial charges contained vinyl acetate (100 mg), sodium acetate as buffer in 0.5 wt % to monomer, sodium dodecyl sulfate (SDS) as surfactant, sodium vinyl sulfonate as stabilizer, Sodium persulfate/metabissulfite as initiator, and water. Surfactant, stabilizer, and initiator were investigated in several different concentrations shown in Table 6. The initial charges were fed at ambient temperature, and then the mixture was maintained at 60° C. followed by continuous feeds (6 hours for vinyl acetate, 7 hours for initiator). After the additions, the reaction was maintained at 60° C. for additional 2 hours. Samples were allowed to cold down to room temperature and then analyzed by GPC, particle size, and GC or $^1$H-NMR. Conditions and Results are in Table 6.

TABLE 6

| | | Polymerization parameters | | | Results | | |
|---|---|---|---|---|---|---|---|
| Example | Control agent | SDS (wt % to monmer) | Sodium persulfate (wt % to monmer) | Sodium Vinyl sulfonate (wt % to monmer) | Conversion (%) | Mn | PDI |
| 64 | Xanthate | 1 | 0.366 | 0.2 | 100 | 16769 | 1.69 |
| 65 | Xanthate | 1.3 | 0.366 | 0.2 | 100 | 16727 | 1.64 |
| 66 | Xanthate | 1.6 | 0.366 | 0.2 | 100 | 16229 | 1.72 |
| 67 | Xanthate | 1 | 0.366 | 0.5 | 100 | 16050 | 1.71 |
| 68 | Xanthate | 1.3 | 0.366 | 0.5 | 100 | 15937 | 1.71 |
| 69 | Xanthate | 1.6 | 0.366 | 0.5 | 100 | 16606 | 1.75 |
| 70 | Xanthate | 1 | 0.407 | 0.2 | 100 | 17191 | 1.72 |
| 71 | Xanthate | 1.3 | 0.407 | 0.2 | 100 | 16288 | 1.62 |
| 72 | Xanthate | 1.6 | 0.407 | 0.2 | 100 | 16527 | 1.64 |
| 73 | Xanthate | 1 | 0.407 | 0.5 | 100 | 16729 | 1.71 |
| 74 | Xanthate | 1.3 | 0.407 | 0.5 | 100 | 16384 | 1.7 |
| 75 | Xanthate | 1.6 | 0.407 | 0.5 | 100 | 15524 | 1.72 |
| 76 | Xanthate | 1 | 0.4553 | 0.2 | 100 | 15855 | 1.73 |
| 77 | Xanthate | 1.3 | 0.4553 | 0.2 | 100 | 18588 | 1.67 |
| 78 | Xanthate | 1.6 | 0.4553 | 0.2 | 100 | 16761 | 1.75 |
| 79 | Xanthate | 1 | 0.4553 | 0.5 | 100 | 16844 | 1.69 |
| 80 | Xanthate | 1.3 | 0.4553 | 0.5 | 100 | 18441 | 1.73 |
| 81 | Xanthate | 1.6 | 0.4553 | 0.5 | 100 | 18357 | 1.64 |
| 82 | Xanthate | 1 | 0.5 | 0.2 | 100 | 18980 | 1.73 |
| 83 | Xanthate | 1.3 | 0.5 | 0.2 | 100 | 18427 | 1.71 |
| 84 | Xanthate | 1.6 | 0.5 | 0.2 | 100 | 17292 | 1.75 |
| 85 | Xanthate | 1 | 0.5 | 0.5 | 100 | 18500 | 1.7 |
| 86 | Xanthate | 1.3 | 0.5 | 0.5 | 100 | 19192 | 1.77 |
| 87 | Xanthate | 1.6 | 0.5 | 0.5 | 100 | 19389 | 1.8 |
| 88 | CT-4 | 1 | 0.366 | 0.2 | 100 | 16464 | 1.48 |
| 89 | CT-4 | 1.6 | 0.366 | 0.2 | 100 | 16135 | 1.47 |
| 90 | CT-4 | 1 | 0.366 | 0.5 | 100 | 14794 | 1.45 |
| 91 | CT-4 | 1.6 | 0.366 | 0.5 | 100 | 15245 | 1.46 |
| 92 | CT-4 | 1 | 0.366 | 0.8 | 100 | 15877 | 1.46 |
| 93 | CT-4 | 1.6 | 0.366 | 0.8 | 100 | 16345 | 1.48 |
| 94 | CT-4 | 1 | 0.407 | 0.2 | 100 | 16721 | 1.49 |
| 95 | CT-4 | 1.6 | 0.407 | 0.2 | 100 | 15780 | 1.46 |

TABLE 6-continued

| | | Polymerization parameters | | | Results | | |
|---|---|---|---|---|---|---|---|
| Example | Control agent | SDS (wt % to monmer) | Sodium persulfate (wt % to monmer) | Sodium Vinyl sulfonate (wt % to monmer) | Conversion (%) | Mn | PDI |
| 96 | CT-4 | 1 | 0.407 | 0.5 | 100 | 15425 | 1.46 |
| 97 | CT-4 | 1.6 | 0.407 | 0.5 | 100 | 14902 | 1.44 |
| 98 | CT-4 | 1 | 0.407 | 0.8 | 100 | 15427 | 1.45 |
| 99 | CT-4 | 1.6 | 0.407 | 0.8 | 100 | 15963 | 1.43 |
| 100 | CT-4 | 1 | 0.4553 | 0.2 | 100 | 16018 | 1.49 |
| 101 | CT-4 | 1.6 | 0.4553 | 0.2 | 100 | 15216 | 1.51 |
| 102 | CT-4 | 1 | 0.4553 | 0.5 | 100 | 15025 | 1.48 |
| 103 | CT-4 | 1.6 | 0.4553 | 0.5 | 100 | 14183 | 1.54 |
| 104 | CT-4 | 1 | 0.4553 | 0.8 | 100 | 14633 | 1.5 |
| 105 | CT-4 | 1.6 | 0.4553 | 0.8 | 100 | 14927 | 1.55 |
| 106 | CT-4 | 1 | 0.5 | 0.2 | 100 | 16291 | 1.57 |
| 107 | CT-4 | 1.6 | 0.5 | 0.2 | 100 | 15785 | 1.54 |
| 108 | CT-4 | 1 | 0.5 | 0.5 | 100 | 15849 | 1.58 |
| 109 | CT-4 | 1.6 | 0.5 | 0.5 | 100 | 15923 | 1.6 |
| 110 | CT-4 | 1 | 0.5 | 0.8 | 100 | 15697 | 1.59 |
| 111 | CT-4 | 1.6 | 0.5 | 0.8 | 100 | 16283 | 1.57 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A method of free radical polymerization comprising (1) forming a mixture of one or more monomers, at least one free radical source and a control agent and (2) subjecting said mixture to polymerization conditions, wherein said control agent is characterized by

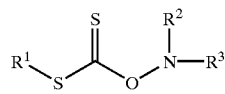

the general formula:
wherein $R^1$ is any group that group that can be expelled as its free radical form in an addition-fragmentation reaction;
$R^2$ and $R^3$ are each independently selected from the group consisting of hydrogen, hydrocarbyl, substituted hydrocarbyl, heteroatom-containing hydrocarbyl, and substituted heteroatom-containing hydrocarbyl, and combinations thereof, and optionally $R^2$ and $R^3$ are joined together in a ring structure having from 3 to 50 atoms in the backbone of the ring; also optionally, $R^2$ and $R^3$ are joined together to form a double bond optionally substituted alkenyl moiety.

2. The method of either of claim 1, wherein an initiator is the source of free radicals.

3. The method of claim 1, wherein $R^1$ is selected from the group consisting of optionally substituted alkyl, optionally substituted aryl, optionally substituted alkenyl, optionally substituted alkoxy, optionally substituted heterocyclyl, optionally substituted alkylthio, optionally substituted amino and optionally substituted polymer chains.

4. The method of claim 3, wherein $R^1$ is selected from the group consisting of —CH$_2$Ph, —CH(CH$_3$)CO$_2$CH$_2$CH$_3$, —CH(CO$_2$CH$_2$CH$_3$)$_2$, —C(CH$_3$)$_2$CN, —CH(Ph)CN, —C(CH$_3$)$_2$Ph, —CH(CH$_3$)CN, and —CH$_2$CH$_2$CH$_2$CH$_3$.

5. The method of claim 1, wherein $R^2$ and $R^3$ are each independently selected from the group consisting of hydrogen, optionally substituted alkyl, optionally substituted aryl, optionally substituted alkenyl, optionally substituted acyl, optionally substituted, aroyl, optionally substituted alkoxy, optionally substituted heteroaryl, optionally substituted heterocyclyl, optionally substituted alkylsulfonyl, optionally substituted alkylsulfinyl, optionally substituted alkylphosphonyl, optionally substituted arylsulfinyl, and optionally substituted arylphosphonyl.

6. The method of claim 1, wherein two or more monomers are added to said polymerization mixture and said two or more monomers are added sequentially or simultaneously.

7. The method of either of claims 1, 2 or 3, wherein said polymerization conditions comprise living kinetics.

8. A polymer formed by the method of claim 1.

9. A method of method of free radical polymerization comprising (1) forming a mixture of one or more monomers, at least one free radical source and a multi-functional control agent and (2) subjecting said mixture to polymerization conditions, wherein said multi-functional control agent is selected from any of the following formulas:

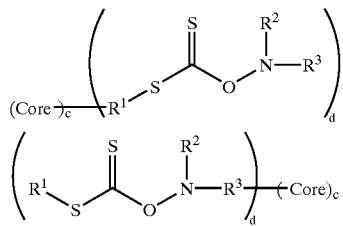

wherein $R^1$ is any group that group that can be expelled as its free radical form in an addition-fragmentation reaction;
$R^2$ and $R^3$ are each independently selected from the group consisting of hydrogen, hydrocarbyl, substituted hydrocarbyl, heteroatom-containing hydrocarbyl, and substituted heteroatom-containing hydrocarbyl, and combinations thereof; and optionally $R^2$ and $R^3$ together to form a double bond optionally substituted alkenyl moiety; and also optionally $R^2$ and $R^3$ together joined in a ring structure having from 3 to 50 atoms in the ring backbone;

Core is a core molecule, and c is 1 or more and d is 2 or more.

10. The method of claim 9, wherein an initiator is the source of free radicals.

11. The method of claim 9, wherein $R^1$ is selected from the group consisting of optionally substituted alkyl, optionally substituted aryl, optionally substituted alkenyl, optionally substituted alkoxy, optionally substituted heterocyclyl, optionally substituted alkylthio, optionally substituted amino and optionally substituted polymer chains.

12. The method of claim 11, wherein $R^1$ is selected from the group consisting of —$CH_2Ph$, —$CH(CH_3)CO_2CH_2CH_3$, —$CH(CO_2CH_2CH_3)_2$, —$C(CH_3)_2CN$, —$CH(Ph)CN$ and —$C(CH_3)_2Ph$, —$CH(CH_3)CN$, —$CH_2CH_2CH_2CH_3$.

13. The method of claim 9, wherein $R^2$ and $R^3$ are each independently selected from the group consisting of hydrogen, optionally substituted alkyl, optionally substituted aryl, optionally substituted alkenyl, optionally substituted acyl, optionally substituted, aroyl, optionally substituted alkoxy, optionally substituted heteroaryl, optionally substituted heterocyclyl, optionally substituted alkylsulfonyl, optionally substituted alkylsulfinyl, optionally substituted alkylphosphonyl, optionally substituted arylsulfinyl, and optionally substituted arylphosphonyl.

14. The method of claim 9, wherein said polymerization conditions comprise a temperature in the range of from about 20° C. to about 110° C.

15. The method of either of claims 1 or 9, wherein two or more monomers are added to said polymerization mixture and said two or more monomers are added sequentially or simultaneously.

16. The method of claim 9, wherein said polymerization conditions comprise living kinetics.

17. A polymer formed by the method of any of claims 9, 10 or 11.

18. The polymer of claim 17, wherein said copolymer is a block copolymer.

19. The polymer of claim 17, wherein said polymer is a star or hyperbranched polymer.

* * * * *